United States Patent
Banks (10) Patent No.: US 7,308,164 B1
(45) Date of Patent: Dec. 11, 2007

(54) METHOD FOR TEXTURING SURFACES OF OPTICAL FIBER SENSORS USED FOR BLOOD GLUCOSE MONITORING

(75) Inventor: Bruce A. Banks, Olmstead Township, OH (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 54 days.

(21) Appl. No.: 11/398,734

(22) Filed: Mar. 30, 2006

Related U.S. Application Data (62) Division of application No. 10/942,637, filed on Sep. 16, 2004, now abandoned.

(51) Int. Cl.
*G02B 6/00* (2006.01)
(52) U.S. Cl. .......................................... 385/12; 385/15
(58) Field of Classification Search ............... None
See application file for complete search history.

(56) References Cited

U.S. PATENT DOCUMENTS

| | | | |
|---|---|---|---|
| 4,935,346 A | 6/1990 | Phillips et al. | |
| 5,320,814 A | 6/1994 | Walt et al. | |
| 5,378,628 A | 1/1995 | Gratzel et al. | |
| 5,859,937 A | 1/1999 | Nomura | |
| 6,200,737 B1 | 3/2001 | Walt et al. | |
| 6,210,910 B1 | 4/2001 | Walt et al. | |
| 6,331,438 B1 | 12/2001 | Aylott et al. | |
| 6,576,101 B1 | 6/2003 | Heller et al. | |
| 6,602,702 B1 | 8/2003 | McDevitt et al. | |
| 6,638,772 B1 | 10/2003 | Douglas et al. | |
| 6,667,159 B1 | 12/2003 | Walt et al. | |
| 7,195,872 B2* | 3/2007 | Agrawal et al. | 435/6 |
| 2003/0032204 A1 | 2/2003 | Walt et al. | |
| 2003/0077205 A1 | 4/2003 | Xu | |

FOREIGN PATENT DOCUMENTS

WO WO 98/45688 10/1998

OTHER PUBLICATIONS

Loh, Ih-Hong, "Plasma Surface Modification in Biomedical Applications", AST Technical Journal, Oct. 2000.*
Bruce A. Banks "Atomic Oxygen Surface Modification Technologies for Biomedical Applications" Presented at NASA Biomedical Conference in Pasadena, California on Feb. 13, 2003.

* cited by examiner

*Primary Examiner*—Sung Pak
(74) *Attorney, Agent, or Firm*—Gary Borda; Robert Rotella (57) ABSTRACT

Disclosed is a method and the resulting product thereof comprising a solid light-conducting fiber with a point of attachment and having a textured surface site consisting a textured distal end prepared by being placed in a vacuum and then subjected to directed hyperthermal beams comprising oxygen ions or atoms. The textured distal end comprises cones or pillars that are spaced upon from each other by less than 1 micron and are extremely suitable to prevent cellular components of blood from entering the valleys between the cones or pillars so as to effectively separate the cellular components in the blood from interfering with optical sensing of the glucose concentration for diabetic patients.

10 Claims, 6 Drawing Sheets

METHOD FOR TEXTURING SURFACES OF OPTICAL FIBER SENSORS USED FOR BLOOD GLUCOSE MONITORING

CROSS REFERENCE TO RELATED APPLICATIONS

This application is a divisional application of parent case Ser. No. 10/942,637 which was filed on Sep. 16, 2004 now abandoned.

ORIGIN OF THE INVENTION

The invention described herein was made by an employee of the United States Government and may be used by or for the Government for governmental purposes without payment of any royalties thereon or therefor.

FIELD OF THE INVENTION

The present invention relates to a sensing device for determination of compounds in fluids, and more particularly, to a solid light-conducting fiber comprising the sensing device with a point of attachment and having a textured surface consisting of a distal end prepared by being placed in a vacuum system and then subjected to directed hyperthermal beams comprising oxygen ions or atoms.

BACKGROUND OF THE INVENTION

The quantification of chemical and biochemical components in aqueous fluids, and particularly in biological fluids such as whole blood or urine and in biological fluid derivatives such as serum and plasma, is of ever increasing importance. Important applications exist in medical diagnosis and treatment and in the quantification of exposure to therapeutic drugs, intoxicants, hazardous chemicals and the like. These applications include the detection and quantification of an increasing variety of certain circulating antibodies, cancer-related metabolites, genetically derived chemical tracers, and hormones emitted during events such as pregnancy. In many instances, the amounts of materials being determined are minuscule in the range of a microgram or less per deciliter.

One common medical test is the measurement of blood glucose levels by diabetics which is more fully described in U.S. Pat. No. 5,859,937 ('937) of H. Nomura and herein incorporated by reference. Portions of the teachings of the '937 patent are used herein for the sake of completeness. The glucose determination, as described in the '937 patent, typically entails the diabetic piercing the skin of his or her finger with a lance, followed by squeezing or expression of a blood droplet. The blood droplet is then transferred to a reagent pad or test strip. The amount of blood that is conveniently expressed from a finger prick is governed by the size and depth of penetration of the lance. Too small a nick results in an inadequately sized blood sample for the intended analysis. Conversely, too deep a nick results in an oversized blood sample. Pain is experienced in the lancing procedure, and the degree of pain is associated with the size and depth of penetration of the lance.

The teachings of the '937 patent provides a textured site allowing for an increased surface area, compared to other prior art devices, for use in blood sampling. The increased surface area provides an advantage relating to minimizing the invasive feature of glucose testing because the surface area being very small, greatly reduces the level of analyte-responsive needed to be deposited to perform the glucose determination. Increased surface area allows one to utilize a small blood droplet, for instance, a droplet having a volume of one (1) to five (5) microliters, or preferably 1 to 2.5 microliters. The '937 patent allows for a reduction relative to the prior art thereof, of about one-fifth to about one-tenth of the fluid volume necessary blood glucose sensing. It is desired that further improvements to the surface area be provided, so as to correspondingly reduce the amount of blood necessary for determination of glucose for diabetics.

The '937 patent provides a textured surface using various means, such as ion beam sputtering, plasma etching including atomic oxygen plasma, physical abrasion, chemical etching, sputtering or ablation by high energy beams, or deposition of dendritic-like structures thereon. The textured surface of the '937 patent is intended to provide a means for separating cellular components in blood from the plasma of the blood so as to allow optical sensing of the glucose concentration in the blood. The processes described in the '937 patent for developing the textured surface need to produce a cone or pillar structure at the ends of optical fibers or other sensing surfaces which are sufficiently close—so as to prevent the cellular components from entering the microscopic valleys between the cones or pillars so that optical sensing of the glucose concentration can be performed. Also, it is desired to have a sufficiently high aspect ratio (height to width) of cones or pillars to allow sufficient surface area for optical determination of the glucose concentration in the blood.

In pursuit for finding desired pillar structures for the textured surfaces, some of the different processes mentioned in the '937 patent were investigated and may be further described with reference to FIG. 1 herein, which illustrates a Scanning Electron Microscope image of the end of a polymethylmethacrylate optical fiber that was textured by the use of thermal energy (<0.5 eV) atomic oxygen through salt dust for enhancing texturing.

Figure 1:
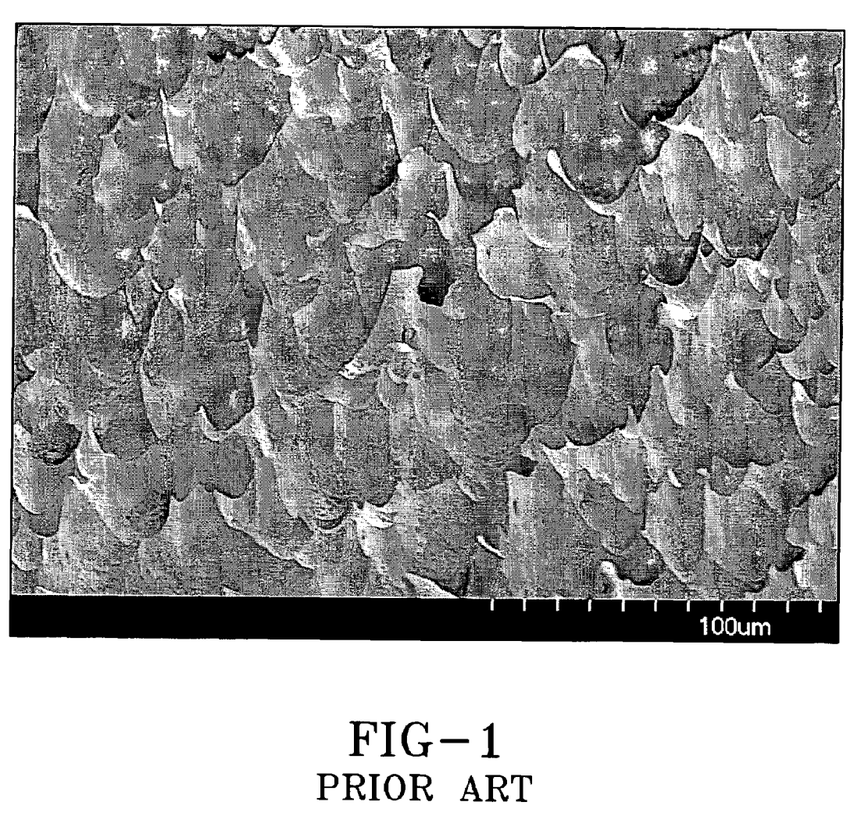
FIG. 1 illustrates a prior art Scanning Electron Microscope image of the end of an optical fiber that was textured by the use of thermal energy (<0.5 eV) atomic oxygen through salt dust to enhance texturing.

The disadvantages of prior art results shown in FIG. 1 is that the craters produced were too wide to prevent cellular blood components from entering the optical sensing areas and the aspect ratio (height to width) of the surface features does not offer high gains in surface area relative to flat surfaces. As can be seen in FIG. 1, the cone or crater ridges are approximately 20-30 microns apart far too much to achieve their desired goals. More particularly, the spacing between cones or ridges needs to be $\leq 5$ microns to block the entry of blood cells into the cone valleys. Thus, the craters did not provide separation of the plasma from the blood in the areas of the valleys between the cones or pillars where optical sensing of the glucose concentration needs to occur. Use of thermal energy (<0.5 eV) atomic oxygen, sometimes referred to as isotropic thermal energy, to texture the surfaces of clear polymers such as polymethylmethacrylate, polystyrene or other hydrocarbon polymer (even with the use of small particle salt shielding) causes wide almost hemispherical craters to form surface features which are only as high as they are wide. The aspect ratio of only approximately one (1) requires greater volume blood samples than desirable. It is desired that textured surfaces for optical sensors used for blood testing be provided that provide cones or pillars that are spaced apart from each other by less than 5 microns, preferably about 1 micron, and having an aspect ratio (height to width) of greater than one (1).

OBJECTS OF THE INVENTION

It is a primary object of the present invention to provide a process that creates a sensor having a textured surface comprising cones or pillars that are spaced apart from each other by less than 5 microns, preferably about 1 micron, and having an aspect ratio of greater than one (1).

Moreover, it is an object of the present invention to provide a process for making fine texture, high aspect ratio cone surface at the distal end of a solid light-conducting fiber that is necessary for optical fiber blood glucose monitoring with small blood samples.

It is a further object of the present invention to provide for an optical sensor having cones or pillars that are sufficiently close so as to prevent cellular blood components for interfering with optical sensing of the blood glucose concentration.

Still further, it is an object of the present invention to provide a process that creates a textured surface for an optical sensing device which has a high surface area that correspondingly allows for a reduction in the amount of blood needed to be removed from a patient so as to reduce the pain to which the patient needs to be subjected for glucose determination.

It is a further object of the present invention to provide for optical polymer devices serving the sensors that may be used for blood plasma diagnostics that require economic separation of plasma in the whole blood for optical sensing measurements.

SUMMARY OF THE INVENTION

The present invention provides for a process that produces a solid light-conducting fiber with a point of attachment and having a distal end possessing a fine texture, high aspect ratio cone surface that provides for optical fiber blood glucose monitoring with small blood samples.

The textured distal end of the solid light-conducting fiber is prepared by being placed in a vacuum and then subjected to direct hyperthermal beams comprising oxygen ions or atoms.

DETAILED DESCRIPTION OF THE PREFERRED EMBODIMENTS

One of the purposes of the present invention is to create a surface on optically transparent polymers which has closely spaced cones or pillars so as to prevent blood cellular components during optical monitoring from entering the valleys between the cones or pillars, which would otherwise interfere with the optical sensing of blood glucose concentration. It is also a purpose of the present invention to produce a high surface area of high aspect-ratio cones or pillars which are taller than they are wide so as to enable glucose sensing with a minimum volume of blood. The cellular components in blood predominantly consist of red blood cells (erythrocytes of 6.6-7.5 microns diameter) and white blood cells (leukocytes such lymphocytes of 8-10 microns diameter, neutrophils of 12-15 microns diameter, eosinophils of 12-15 microns diameter, basophils of 9-10 microns diameter and monocytes of 16-20 microns diameter). Thus, a 5 micron average spacing between cones or pillars would serve to prevent the cellular components of blood from entering the valleys between the cones and pillars which needs to be occupied by the plasma only so as to prevent optical obstruction of the glucose sensing by light emitted from the sides of the cones on the textured optical fiber end in a manner to be described hereinafter. A further enhancement is provided by having the spacing between cones or pillars be about 1 micron. A high aspect ratio of the texture (cone height to cone separation) provides a greater surface area, thus enabling a smaller volume blood needed to measure glucose concentration. The invention may be further described with reference to prior art shown in FIG. 2.

Figure 2:
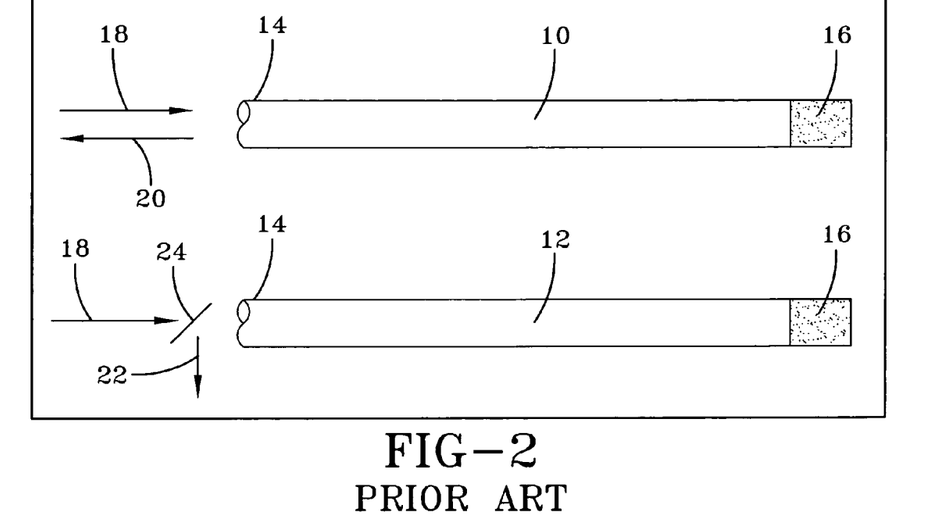
FIG. 2 is a prior art schematic view of fibers with textured surface sites.

FIG. 2 illustrates two solid light-conducting fibers 10, and 12 each being transparent, each having a point of attachment 14, and each preferably comprised of a polymer material, except for silicone. Each of the fibers 10, and 12 has a textured surface 16 at the distal end thereof that is provided by one of the processes of the present invention to be further described hereinafter with reference to FIG. 5-8.

In one application, at least one end, that is point of attachment 14, of the light-conductive fibers 10 or 12, is placed adjacent to a light source (not shown) for sending a beam of light 18 down the fiber length. The point of attachment 14 of each of the fibers 10 and 12 is also located adjacent to a device for measuring light beam characteristics of light 20 or 22 emanating from the fibers 10 or 12, respectively after being reflected by the distal end 16. For fiber 12, a device 24 may be employed to intercept the returning light beam 22 and reflect the light beam 22 downward, as shown in FIG. 2. When the point of attachment 14 is to be adjacent to both the light source and the device for measuring the light beam characteristics, light measurement is dependent upon reflection of the light beam, such as light beam 22, by device 24 as shown for fiber 14.

The textured surface 16 may be treated so as to contain an analyte responsive reagent (not shown in FIG. 1). A chemiluminescent or fluorescent reaction at the textured site 16 resulting from reagent-analyte interactions can be advantageously utilized wherein a portion of the chemiluminescent or fluorescent light enters the fiber 10 or 12, and is transmitted to a device such as a luminometer, located at one end of the fiber 10, or 12, for detection and quantitation. The textured surfaces 16 may be further described with reference to prior art shown in FIG. 3.

Figure 3:
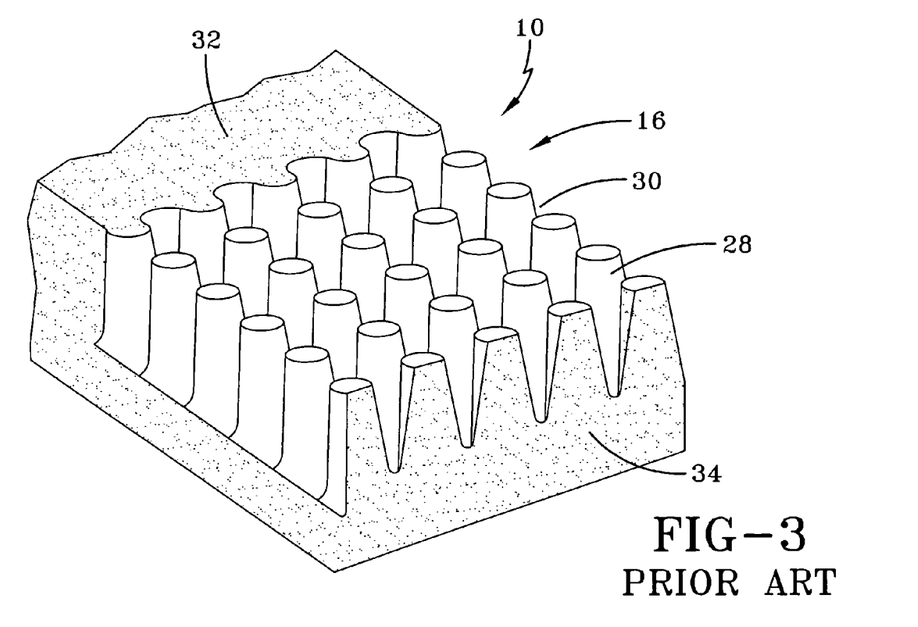
FIG. 3 is a prior art schematic view of a cone field within a textured surface of an optic fiber.

FIG. 3 provides an enlarged view of a cutaway section of a fiber 10 having a textured surface 16. The textured surface 16 is schematically depicted in this case as an array of cone-shaped projections or pillars 28 defining a cone field 30, which has been formed within the surface 32 of a fiber by removal of portions of surface 32 and subsurface 34 material. Further details of the textured surface 16 may be further described with reference to prior art in FIG. 4.

Figure 4:
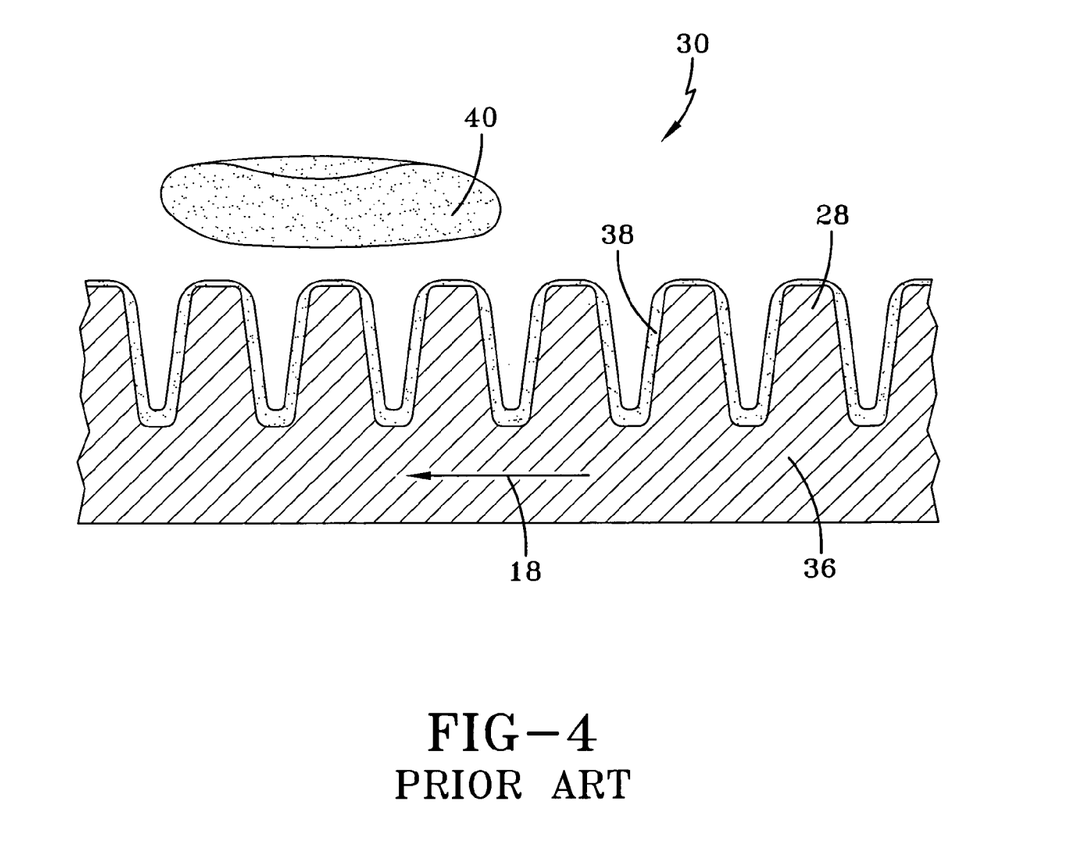
FIG. 4 is a prior art cross-section of a cone field with the deposited reagent, along with adjacent erythrocyte.

FIG. 4 shows a representative cross-section 36 of the cone field 30, wherein a deposit 38 of the analyte-responsive reagent has been conventionally placed within the crevices between cone projections 28. Also shown in FIG. 4 is a representation of an erythrocyte 40 (a red blood cell), whose size in relationship to the openings between the cones of the cone field is large, such that it can typically make no more than incidental contact with the outermost projections of the cones 28. In a determination of a small analyte, such as glucose, the reagent deposit 38 within the cone field 30 is readily accessed by the analyte, but protected from the erythrocytes 40 based on size selection by the cone field 30 pattern. Changes in the reagent deposit 38, such as by development of a colored complex through reaction with an analyte, is advantageously detected by means of a light beam (indicated by the arrow 18) being transmitted through the matrix of the fiber. The textured surface 16 is generally in the form of conical or ridge-like structure microns high and wide having a desired aspect ratio (length/wide) which is preferably greater than one (1). The term "cone field" is herein defined to include textures, which are not necessarily in the specific shape of cones, but may include various linear, box-like or angular arrays of projections so long as their aspect ratio is greater than one (1).

The analytic-responsive reagent 38 placed between the crevices of the cones or pillars 28 may be one of many analyte-sensing systems. In a manner known in the art, for blood glucose determinations, the analyte-sensing system is preferably a composition including a peroxidase enzyme and color-generating chemical couplers. Many combinations of such chemical systems for blood glucose determinations are disclosed and described in U.S. Pat. No. 4,935,346, which is herein incorporated by reference. For antigens, antibodies, enzymes, enzyme inhibitors, and various other biochemical agents, attachment of affinity ligands to the textured surface 16 may be practiced. Herein, the light traveling through the fiber is affected by the development of resulting affinity complexes on the textured fiber surface 16. Alternatively, chemiluminescent or fluorescent techniques may be utilized to highlight the affinity attachment of specific biomolecules on the textured surface, a portion of the chemiluminescent or fluorescent light being captured and transmitted through the fiber to a detector. Attachment of ligands to polymeric surfaces through covalent binding is well known in the art of affinity membranes.

In a preferred method of use of the invention, a light-conducting fiber, such as 10 of FIG. 2, having a textured site 16 thereon is located at attachment point 14 adjacent to a light source for transmittal of a light beam 18 into the fiber 10, and adjacent also to a device for analysis of light beam characteristics of light beam 20 emanating from an opposite end of the fiber 10 after it is reflected by the textured site 16. In a most preferred embodiment, both light input and emanation thereof are at one end of a fiber 10 of predetermined length, and the textured site 16 is at an opposite end of the fiber 16. The textured surface site 16 is first impregnated with an analyte responsive reagent, such as a plasma coated analyte. The textured site 16, is then wetted with a fluid, such as by contacting the fiber at this site 16 with a small droplet of blood. Interaction of the reagent with the analyte, if any, present in the fluid is allowed to occur, resulting in an observable physical or chemical change at the textured site 16. Light passing through the fiber 10 in the region of the textured site 16 is altered in its characteristics such as frequency and amplitude, one or more of these changes being detectable and preferably quantifiable by the device utilized for analysis of light beam 20 emanating from the fiber. More particularly, light intercepting the textured surface 16 creates a change in the spectral reflectance as a result of the light interacting with the plasma-coated analyte surface 16.

Thus, as known in the art, a diabetic patient wishing to measure his or her blood glucose level would pierce the skin of a finger with a lancet whose size and depth of penetration is designed to provide a minimally sized droplet, to be further described hereinafter, of blood at a minimized level of associated pain. The patient would preferably then touch a textured site 16 to the droplet, the fiber being advantageously pre-fixed to a measurement device. The patient would then read and record his or her blood glucose concentration determined upon wetout of the textured surface site 16 by the minimally sized blood droplet. The minimally sized droplet is to be further described hereinafter. The preparation of the textured surface 16 is of particular importance to the present invention and may be further described with reference to FIGS. 5-8.

One of the main contributions of the present invention is to provide ability to the art to make pillars and cones 28 much closer together than any prior art has been able to demonstrate. Also, the present invention provides for the use of directed hyperthermal beams comprised of oxygen atoms or ions to make the aspect ratio high, which gives the art of measuring fluid samples a much greater effective surface area relative to prior art techniques, in the form of the textured surface 16 to receive the fluid samples.

Figure 5:
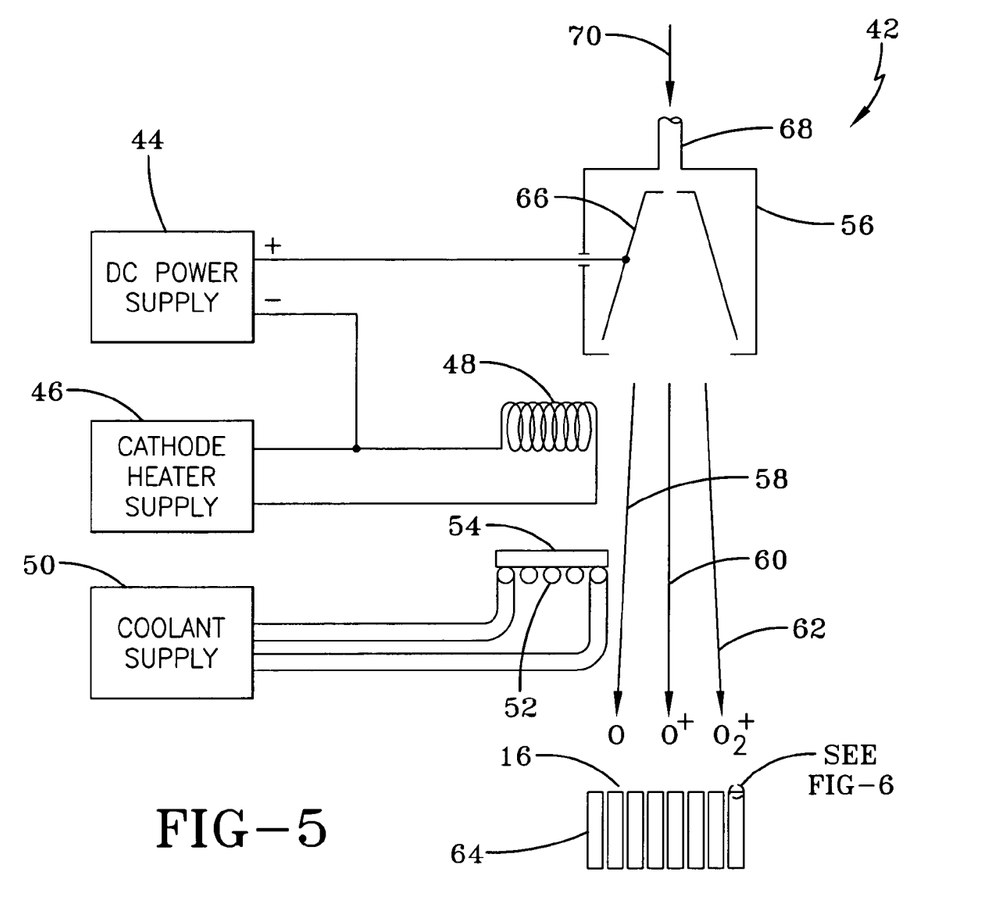
FIG. 5 is a block diagram of a process that provides hypothermal ionic or atomic oxygen texturing of optical surfaces.
Figure 7:
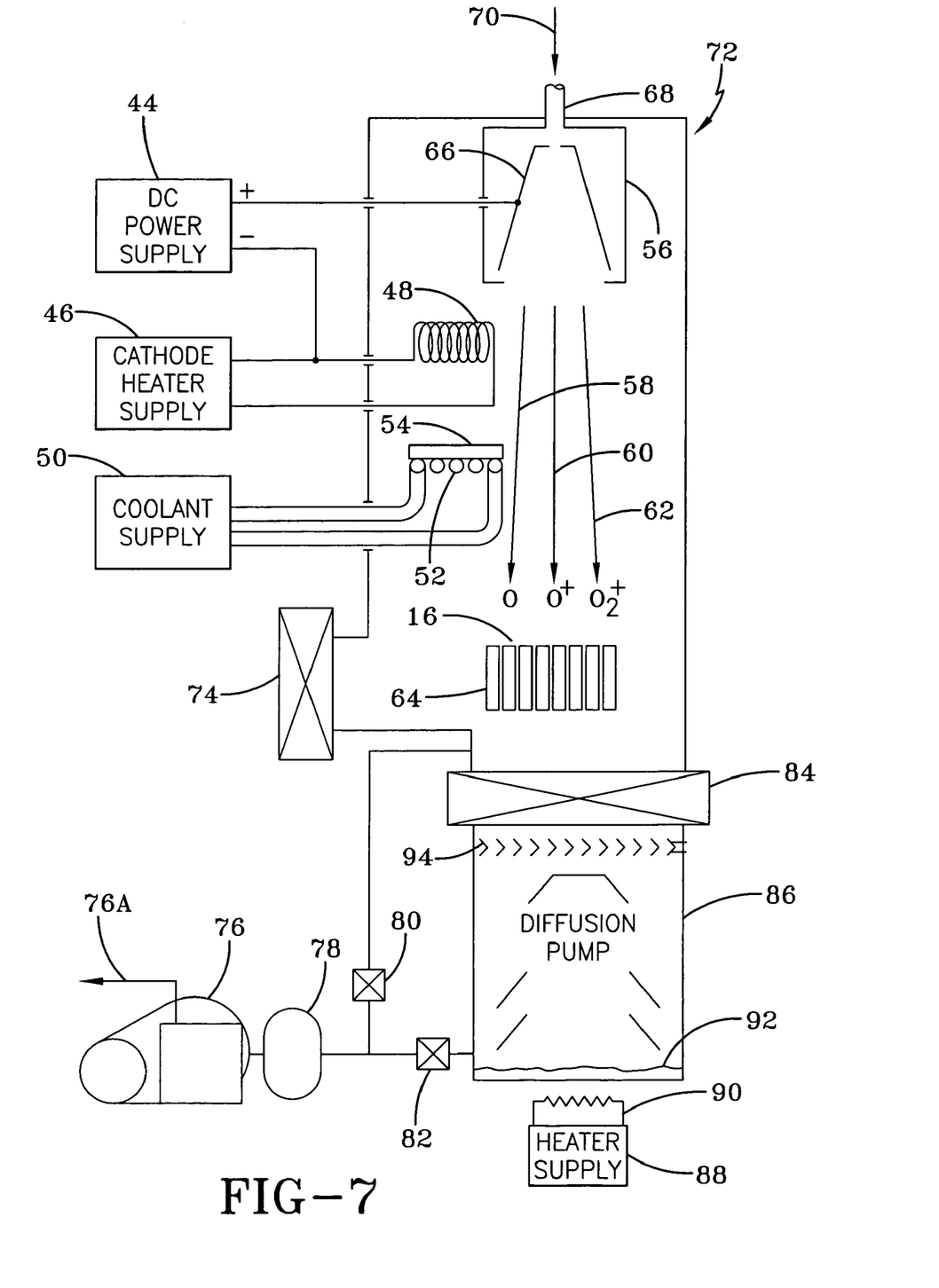
FIG. 7 is a block diagram of the apparatus that provides the desired process of the present invention.
Figure 8:
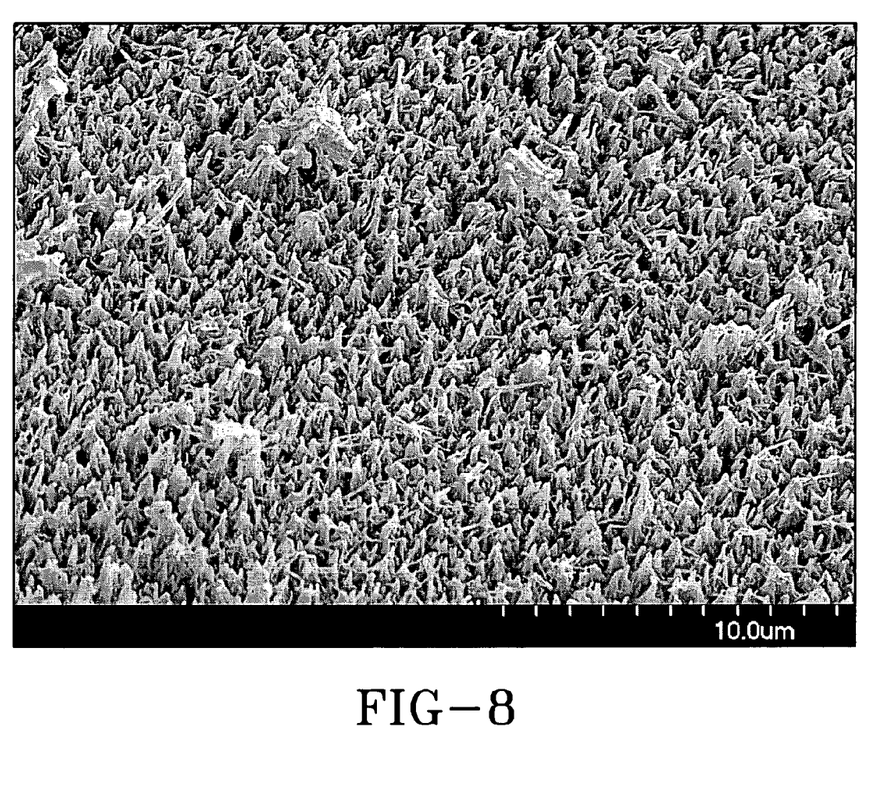
FIG. 8 is a Scanning Electron Microscope image of an atomic oxygen textured optical fiber of the present invention that was textured by means of End Hall atomic or ionic oxygen sources which produced hyperthermal (>1 eV) atomic oxygen ions.

In general, the arrangements shown in FIGS. 5 and 7 provide one or more processes used to produce closely-spaced high aspect-ratio cones or pillars 28, as shown in FIG. 8, to be further described hereinafter, in optically clear polymers consisting of exposing the surfaces of the polymers to be textured to a directed beam of energetic atomic oxygen atoms or ions. The energy of the atomic oxygen atoms or ions should be hyperthermal (>1 eV) so as to produce the textured surfaces shown in FIG. 8, rather than isotropic thermal energy (<0.5 eV), selected by prior art methods, that disadvantageously cause directed atomic oxygen reaction with hydrocarbon atoms that make up the polymer of the fiber and disadvantageously produce the prior art surfaces shown in FIG. 1.

In the practice of the present invention, it was determined that the energy level desired was greater than 1 eV. It was further determined that the preferred range was energies in the range of 50 to 100 eV. So although it is desired to use energy levels of greater than 1 eV, the typical range of energies used to actually do the texturing, which work best in terms of high length-to-width cones 28, is in the 50 eV to 100 eV range.

The reactions, provided by the present invention, produce closely-spaced high aspect-ratio cones or pillars. To perform this process one must place the optical polymers to be textured in a vacuum system, which evacuated to $\leq 1 \times 10^{-5}$ torr. Without the vacuum system atomic and ionic oxygen may be attenuated such as that which occurs at high pressure such as air pressure. An energetic (>1 eV) beam of atomic oxygen atoms or ions is then formed in the vacuum system by ion or atom beam accelerating devices, such as End Hall ion accelerators, electron bombardment ion thrusters or other electrostatic, electromagnetic or arc devices, to be further described hereinafter. These different sources need to be able to produce oxygen ion or atom energies of greater than 1 eV.

As known in the art, the resulting beams developed from the source of greater than 1 eV are directed hyperthermal beams. In one embodiment, the ends of thousand of optical fibers can be treated at one time. An arrangement 42 of the apparatus for the desired processes is shown in FIG. 5, which is devoid, for the sake of clarity, of the desired vacuum source, which will be further described hereinafter with reference to FIG. 7.

The arrangement 42 of FIG. 5 comprises a DC power supply 44 having a preferred range of 25-150 volts, a cathode heater supply 46 connected to a cathode 48, and a cooling supply 50 preferably being of water and connected to a water cooling coil 52 arranged with a water-cooled radiation shield 54.

The arrangement 42 further comprises a hyperthermal atomic oxygen source 56 that can be any source of oxygen atoms or ions that produce a directed beam of energy greater than 1 eV and shown as beams 58, 60, or 62 and indicated as 0, $0^+$, $O_2^+$ respectively. The ions in the beams 58, 60, and 62 can be single or multiply charged. The ionic or atomic source 56 can be an End Hall source, an electron bombardment ion source, a DC plasma source, a microwave plasma source or any other source provided the source delivers a hyperthermal beam of greater than 1.0V comprised of oxygen atoms or ions.

The positive terminal of the DC power supply 44 is connected to an anode 66 of the source 56, whereas the negative terminal of the DC power supply 44 is connected to the cathode 48. The directed hyperthermal beams 58, 60, and 62 are preferably directed from one direction onto the distal end 16 of each of the light-conducting fibers of the bundle 64, so as to produce the textured surface 16 thereon, which may be further described with reference to FIG. 6.

Figure 6:
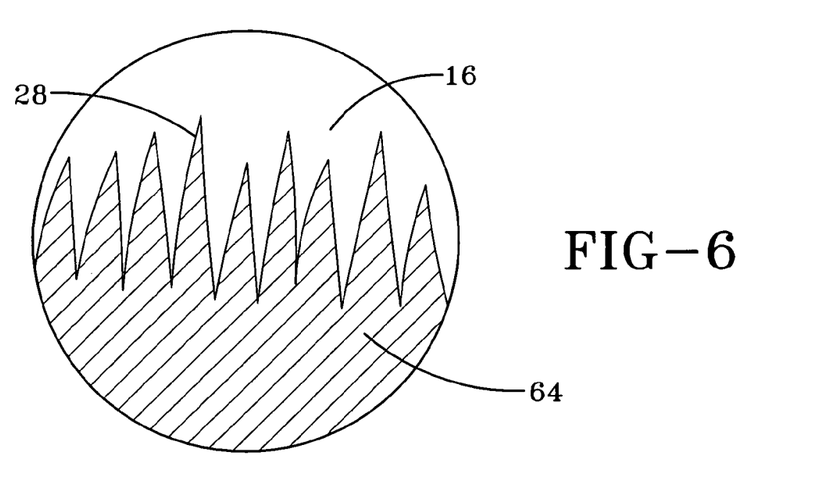
FIG. 6 is an enlarged view of the cones or pillars of the textured surfaces provided by the embodiment of FIG. 5.

FIG. 6 shows the textured surface as comprising the cones 28 that are separated from each other by distance no less than 1 micron and have an aspect ratio (length/width) that is in the range of from about 1 to about 6.

The distance between the source 56 and the bundle 64 of optical fiber can be varied from 3 cm to 200 cm provided the atom or ion beam 58, 60, and 62 does not become depleted by scattering, in a manner known in the art, from background oxygen gas molecules in a vacuum chamber, to be further described hereinafter with reference to FIG. 7. The thermal shield 54 is used to prevent sensitive optical fibers, such as those comprised in bundle 64, from melting. The shield 54 may be a water-cooled shield or may comprise a multi-layer insulation or even eliminated if the End Hall source 56 uses a hollow cathode 66 and does not produce much thermal radiation. For such an arrangement, the optical fibers do not need to be relatively close to the End Hall source 56, and if the optical fibers are farther away there is less cooling needed thereof.

The bundle 64 is preferably brought together so as to provide a hexagonal close-packed array so that the directed atomic oxygen or ion beam 58, 60, or 62 impinges on the end surface of all the fibers, that is the distal end 16 thereof, at once so as to produce the textured surface 16 of all of the fibers making up the bundle 64. The atomic oxygen source 56 may cause heating of the optical bundle 64. To prevent the heat sensitive polymers, such as polymethylmethacrylat from melting, the water cooled or thermal-shield chill 54 is inserted between the End Hall cathode 66 and the optical fiber bundle 64, as shown in FIG. 5.

In general, the length of the cones 28 and the spacing between the cones 28, can be varied by simply changing the fluence (atomic and ionic oxygen exposure level). The length and height have been found to grow in proportion to the square root of the fluence (known in the art). The vacuum source in which the bundle 64 of solid light-conducting fibers are placed before being subjected to the hyperthermal beams 58, 60, or 62, may be further described with reference to FIG. 7.

FIG. 7 shows a vacuum source 72 having a door 74 through which the bundle 64 of fibers may be entered. The vacuum source 72 can be any configuration that allows evacuation down to a pressure of less than $1 \times 10^{-5}$ torr during atomic oxygen operation.

The vacuum source 72 shows provisions of a roughing pump 76 that provides an output to a blower pump 78 which, in turn, provides an output source of air to valves 80 and 82, all in a manner known in the art. The valve 80 directs its output into the vacuum source 72 by way of gate valve 84, whereas the valve 82 directs its output into a diffusion pump 86 (also known in the art).

The diffusion pump 86 receives heat from a heat supply 88 by way of elements 90 and 92. The diffusion pump 86 also receives cooling ($LN_2$) by means of a liquid nitrogen cooled trap 94.

The apparatus of FIG. 7, using conventional elements, provides for one method of the present invention that causes a solid light-conducting fiber used in the analyses of blood and to have a desired textured surface 16 by first placing the solid light-conducting fibers 10 or 12 having the distal end 16 in a vacuum source 72 and then subjecting the distal end 16 to directed hyperthermal beams 58, 60, or 62 comprising oxygen atoms or ions. The operation of the apparatus of FIG. 7 provides for textured surface 16, which may be further described with reference to FIG. 8.

FIG. 8 shows a Scanning Electron Microscope image of an atomic oxygen textured polymethgylmethacrylate optical fiber that was textured by the practice of the present invention using a hyperthermal (>1 eV) End Hall atomic or ionic oxygen source provided by the apparatus of FIG. 7. FIG. 8 shows that the separation between pillars and cones is $\leq 1$ micron and extremely thus suitable to prevent the cellular components of blood from entering the valleys between the cones or pillars 28 shown in FIG. 4. In addition, the aspect ratio of the fibers is much greater than 1, far better than the aspect ratio of less than one (1) achieved by the thermal energy atomic oxygen texturing shown in FIG. 1.

One of the primary advantages of the present invention, relating to its minimally invasive feature, is the presence of a large surface area in a very small, localized area, by which a greatly increased level of analyte-responsive reagent can be deposited and maintained. As more fully described in the previously incorporated by reference '937 patent, the large surface area disclosed in the '937 patent allows for the accommodation of blood samples preferably in the range of 1.0 to 2.5 microliters. Based on the practice of the present invention, a ratio of 2 to about 6 increase in effective area relative to the teaching of the '937 patent is achieved which, in turn, decreases the amount of blood sample required by a factor of 2 to about 6. Thus, the practice of the present invention accommodates a blood sample in the range from about 0.5 to 1.25 microliters to about from 0.16 to about 0.41.

It should now be appreciated that the practice of the present invention provides for the use of directed hyperthermal equal or greater than 1 eV beams comprising oxygen atoms or ions to produce textured surfaces 16. The present invention also provides for the thermal radiation shielding to prevent overheating of the textured surfaces, while at the same time, one embodiment uses an End Hall atomic or ionic oxygen source, having a hollow cathode, and providing for texturing optical polymer surfaces without the use of thermal shielding.

The present invention makes use of the natural formation of cones or pillars that result in direct hyperthermal (greater than 1 eV) atomic or ionic oxidation of polymers. The apparatus of the present invention allows these cones or pillars 28 to be sufficiently close or spaced so as to prevent cellular blood components from interfering with optical sensing of blood glucose concentration. The present invention also provides for small samples of blood to be used as compared to the previous prior art sensors performing the same task.

While the present invention has been described more particularly in the context of glucose determinations and whole blood by diabetics, the invention may be utilized in the determination of other analytes as well, or as even simultaneous determination of two or more analytes.

While the preferred invention is presently contemplated that has been shown in the drawing as described herein, variations of preferred embodiments will be apparent to those skilled in the art and the invention should not be construed as limited to the specific forms as shown and described herein, but rather set forth in the following claims.

I claim:

1. A method of producing a solid light-conducting fiber used in the analysis of a blood comprising the steps of:
   a) placing at least one solid light-conducting fiber with a point of attachment and having a distal end in a vacuum source; and
   b) subjecting said distal end to directed hyperthermal beams comprising oxygen ions or atoms.

2. The method according to claim 1, wherein said vacuum source supplies a pressure of less than about $1 \times 10^{-5}$ while said distal end is being subjected to said directed hyperthermal beams comprising oxygen ions or atoms.

3. The method according to claim 1, wherein said directed hyperthermal beams have an energy level that is in the range from about greater than 1 eV to about 100 eV.

4. The method according to claim 3, wherein said directed hyperthermal beams is in the range from about 50 eV to about 100 eV.

5. The method of claim 1, wherein said directed hyperthermal beams comprising oxygen ions or atoms are provided from a source selected from the group consisting of an End Hall source, an electron bombardment ion source, a microwave plasma source and an arc source.

6. The method according to claim 5, wherein said selected source and said distal end are spaced apart from each other by a distance in the range from about 3 cm to about 200 cm.

7. The method according to claim 5, wherein said at least one solid light-conducting fiber comprises a plurality arranged in a bundle and each having a distal end.

8. A method of producing a solid light-conducting fiber used in the analysis of a blood comprising the steps of:
   a) placing a plurality of light-conducting fibers arranged in a bundle in a vacuum source, each light-conducting fiber having a point of attachment and a distal end; and
   b) subjecting said distal end to directed hyperthermal beams comprising oxygen ions or atoms, wherein said directed hyperthermal beams comprising oxygen ions or atoms are provided from a source selected from the group consisting of an End Hall source, an electron bombardment ion source, a microwave plasma source and an arc source and, wherein said selected source and said bundle have a shield interposed therebetween and wherein said selected source and said distal ends of said bundle are spaced apart from each other by a distance in the range from about 3 cm to about 200 cm.

9. The method according to claim 8, wherein said shield is selected from the group consisting of a water-cooled shield and multilayer insulation shield.

10. The method according to claim 7, wherein said source is an End Hall source having a hollow cathode and separated from said distal ends of said bundle by a distance in the range from about 3 cm to about 200 cm.

* * * * *